United States Patent [19]
Leifeld et al.

[11] Patent Number: 5,930,870
[45] Date of Patent: Aug. 3, 1999

[54] MEASURING FIBER LENGTH AT INPUT AND OUTPUT OF A FIBER PROCESSING MACHINE

[75] Inventors: Ferdinand Leifeld, Kempen; Stefan Schlichter, Viersen, both of Germany

[73] Assignee: Trützschler GmbH & Co. KG, Mönchengladbach, Germany

[21] Appl. No.: 08/988,166

[22] Filed: Dec. 10, 1997

[30] Foreign Application Priority Data

Dec. 13, 1996 [DE] Germany .............................. 196 51 891

[51] Int. Cl.⁶ .................................................. D01G 15/46
[52] U.S. Cl. ............................................ 19/105; 19/106 R
[58] Field of Search .................................. 19/105, 106 R, 19/108, 239, 240, 296, 65 R, 200; 356/237–239; 364/470.01

[56] References Cited

U.S. PATENT DOCUMENTS

| | | |
|---|---|---|
| 4,854,011 | 8/1989 | Stäheli et al. . |
| 4,858,277 | 8/1989 | Pinto et al. ............................ 19/105 X |
| 5,282,141 | 1/1994 | Faas et al. .............................. 19/105 X |
| 5,410,401 | 4/1995 | Shofner et al. .......................... 356/238 |
| 5,692,267 | 12/1997 | Leifeld .................................. 19/106 R |
| 5,805,452 | 9/1998 | Anthony et al. .................... 364/470.13 |

FOREIGN PATENT DOCUMENTS

| | | |
|---|---|---|
| 0 410 429 | 1/1991 | European Pat. Off. . |
| 40 18 803 | 12/1991 | Germany . |
| 41 30 184 | 4/1995 | Germany . |
| 32 18 114 | 10/1995 | Germany . |
| 627 498 | 1/1982 | Switzerland . |
| 2 019 913 | 11/1979 | United Kingdom . |

OTHER PUBLICATIONS

Koch et al, Grosses Textil–Lexikon, L–Z, Deutsche Verlags–Anstalt, Stuttgart, 1966, pp. 415, 416.

*Primary Examiner*—Ismael Izaguirre
*Attorney, Agent, or Firm*—Venable; Gabor J. Kelemen

[57] ABSTRACT

A method of measuring fiber while being processed by a fiber processing machine, includes the following steps: measuring the length of fiber at an inlet of the fiber processing machine; measuring the length of fiber at an outlet of the fiber processing machine; and forming a difference between the values measured at the inlet and the values measured at the outlet for determining an extent of shortening to which the fiber is subjected as the fiber passes through the fiber processing machine.

20 Claims, 4 Drawing Sheets

MEASURING FIBER LENGTH AT INPUT AND OUTPUT OF A FIBER PROCESSING MACHINE

CROSS REFERENCE TO RELATED APPLICATION

This application claims the priority of German Application No. 196 51 891.1 filed Dec. 13, 1996, which is incorporated herein by reference.

BACKGROUND OF THE INVENTION

This invention relates to a method and an apparatus for its practice, integrated in a carding machine, a roller card unit or a similar fiber processing machine. The apparatus is of the known type in which the staple (fiber length) in the fiber mass is measured at the output of the machine (hereafter carding machine), and regulation is effected based on the sensed signals.

In a known process as disclosed in published European Patent Application No. 0 410 429, at the output of the carding machine the staple is measured; the measured values must correspond to precisely defined criteria. If it is not feasible to maintain such values within the predetermined magnitudes by regulating the carding machine, an attempt is first made to improve such values by setting the fine cleaning machine anew. If again, such an attempt is unsuccessful, it is necessary to change the mixing ratio which has to be performed by an appropriate control of the bale opener; this also affects the bale stock. In such a process the staple is measured only at the output of the carding machine. It is a disadvantage of such an arrangement that an accurate prediction concerning the shortening of staple by the carding machine is not possible. It is a further drawback that in the known process the basic assumption is that an improvement of the staple in the carding machine itself is not possible, but can be remedied essentially only by changing the mixing ratio.

SUMMARY OF THE INVENTION

It is an object of the invention to provide an improved method and apparatus from which the discussed disadvantages are eliminated and which significantly reduces fiber damage (fiber shortening) by the carding machine.

This object and others to become apparent as the specification progresses, are accomplished by the invention, according to which, briefly stated, the method of measuring fiber while being processed by a fiber processing machine includes the following steps: measuring the length of fiber at an inlet of the fiber processing machine; measuring the length of fiber at an outlet of the fiber processing machine; and forming a difference between the values measured at the inlet and the values measured at the outlet for determining an extent of shortening of the fiber as it passes through the fiber processing machine.

The measures according to the invention permit a prediction concerning a staple shortening by the carding machine. In this manner fiber damage (fiber shortening) may be significantly reduced by the setting of the working elements of the carding machine.

The invention has the following additional advantageous features:

A partial quantity is taken in which the fiber lengths are measured.

A partial quantity is taken from the fiber material and the length of the fibers of the partial quantity is measured.

For measuring the fiber lengths a small fiber quantity is drawn off by suction at the inlet and/or the outlet of the carding machine. Such a suction effect is reinforced by a stream of compressed air.

The length of fiber is determined from the fiber material at the doffer or the stripper roll or in the zone upstream or downstream of the crushing rolls or at a licker-in.

Data for a staple diagram are obtained from the measured values representing fiber lengths.

The removal of partial fiber quantities and the measurement of the fiber lengths are carried out automatically.

The measuring values for the staple are inputted in the control and regulating device and further, from the inputted data optimized machine setting data are obtained and, as a function thereof, at least one working element of the carding machine is set for affecting the staple.

The working element changes the carding intensity.

The distance between the clothing of the carding cylinder and the clothings of the traveling and/or stationary flats is varied.

The fiber length in the fiber material is measured upstream and downstream of the main carding cylinder.

The dependency of the staple length from the setting of the working element is utilized for more than one fiber quality.

The inputted staple data are compared with the stored characteristic curve.

Further according to the invention a fiber processing machine such as a carding machine, a roller card unit or the like for processing textile fibers such as cotton, chemical fibers and the like is provided, wherein at the outlet of the machine (also collectively referred to as carding machine) the staple (fiber length) in the fiber mass is measurable and a regulation for the carding machine is provided in which the staple (fiber length) is also measurable at the inlet of the carding machine and further, from the measuring values determined at the inlet and the outlet, differential values are formed representing the shortening of the fiber.

The fiber processing machine according to the invention has the following additional advantageous features:

The staple is measurable on-line.

A sensor detecting shortened fiber is provided.

A fibrograph is provided for the measurement of the fiber length distribution.

For measuring the fiber length means are provided for drawing away by suction a small quantity of fiber at the input and/or at the output of the carding machine.

An electronic control and regulating device such as a microcomputer is provided which is connected to a measuring device for the staple and a setting member for a work element of the carding machine for affecting the staple.

Means are provided for obtaining electrical signals from the measured values.

The setting member is an actuator for setting the flexible bend of the carding machine.

DESCRIPTION OF THE PREFERRED EMBODIMENTS

Figure 1:
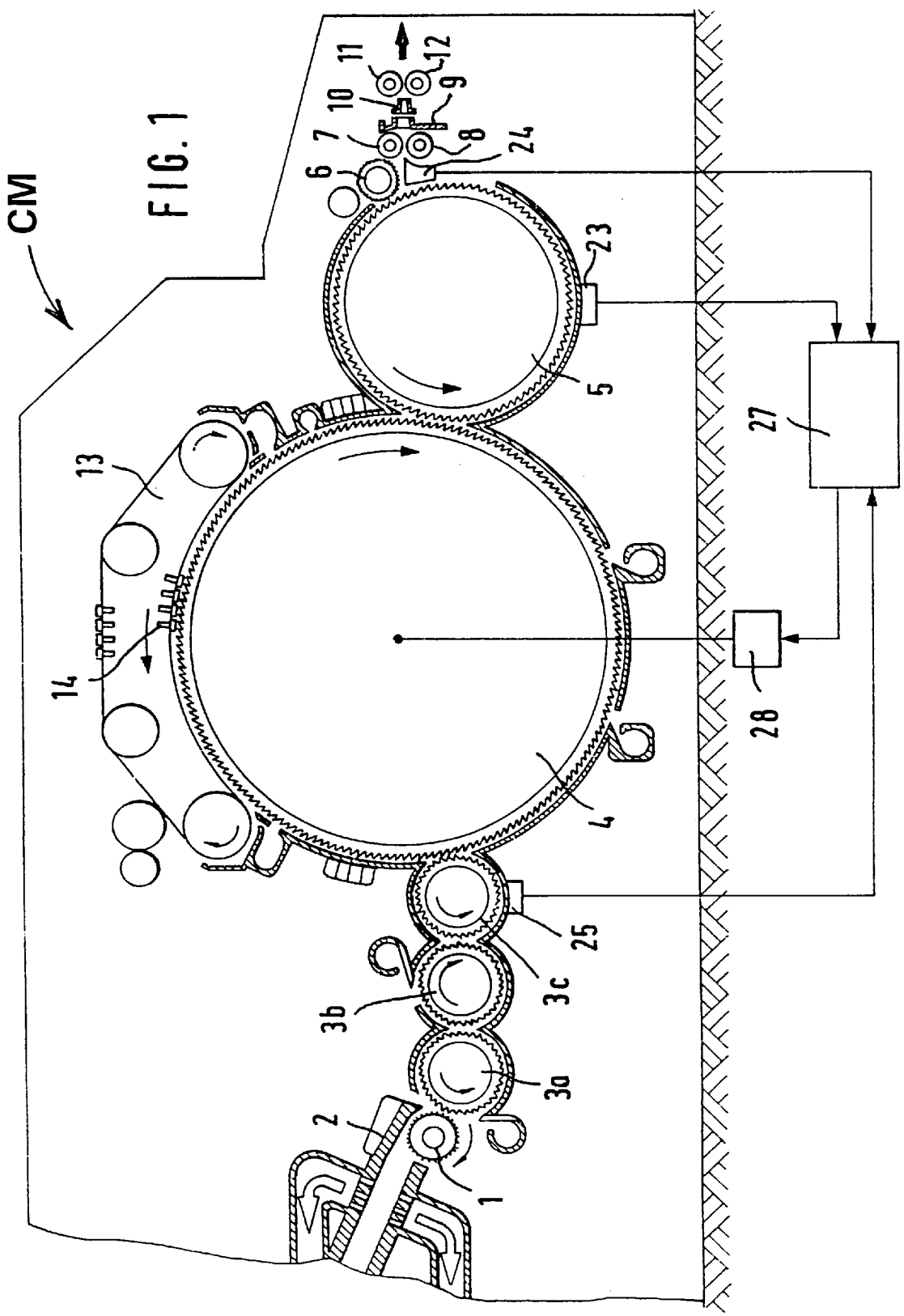
FIG. 1 is a schematic side elevational view of a carding machine incorporating the apparatus according to the invention.

FIG. 1 illustrates a carding machine CM which may be an EXACTACARD DK 803 model, manufactured by Trützschler GmbH & Co. KG, Mönchengladbach, Germany. The carding machine CM has a feed roller 1, a feed table 2 cooperating therewith, licker-ins 3a, 3b, 3c, a main carding cylinder 4, a doffer 5, a stripping roll 6, a pair of cooperating crushing rolls 7, 8, a web guiding element 9, a sliver trumpet 10, a pair of cooperating calender rolls 11, 12 and traveling flats 13 including flat bars 14.

Underneath the doffer 5 a measuring element 23 (sensor) is positioned for measuring the fiber lengths (staple) and underneath the stripping roll 6 a measuring element 24 is arranged for detecting the nep number of the fiber web. Underneath the licker-in 3c a measuring element 25 is situated for detecting fiber lengths. The measuring elements 23, 24 and 25 are connected with an electronic control and regulating device 27, such as a microcomputer, an output of which is coupled to an rpm-regulated motor 28 for driving the main carding cylinder 4. The direction of rotation of the various rolls and rollers is indicated by respective curved arrows.

Figure 2:
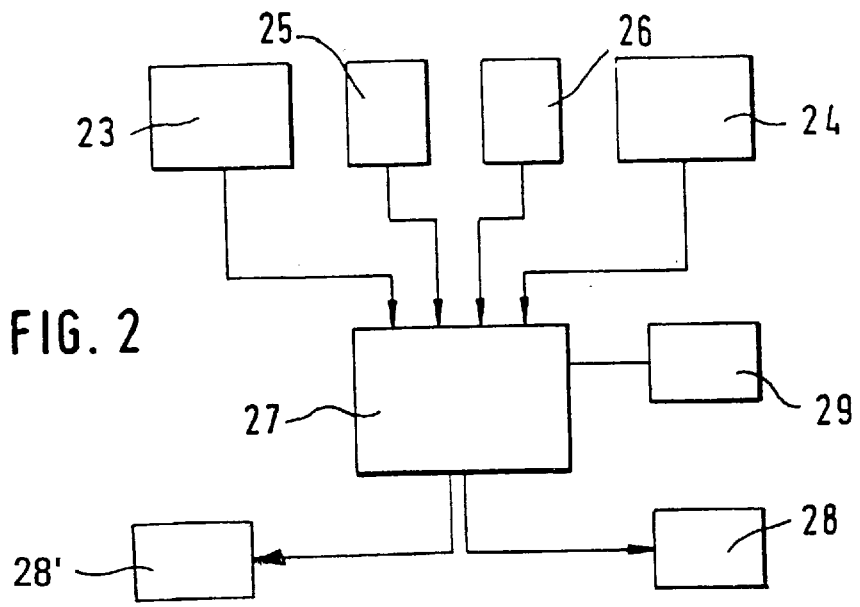
FIG. 2 is a block diagram of an electronic control and regulating device to which at least a nep sensor, a fiber length sensor and a control device, such as a motor are connected.

As shown in FIG. 2, to the control and regulating device 27 there are connected the measuring member 23, the measuring member 24, the measuring member 25 for detecting the fiber lengths at the input of the carding machine, for example, at the licker-in 3c, a measuring member 26 for detecting the nep number at the input of the carding machine, a desired value setting device 29, the drive motor 28 of the carding cylinder 4 and a motor 28' which varies the distance between the clothings of the flat bars 14 and the clothing of the main carding cylinder 4 (see FIG. 6) and thus alters the carding intensity.

Figure 6:
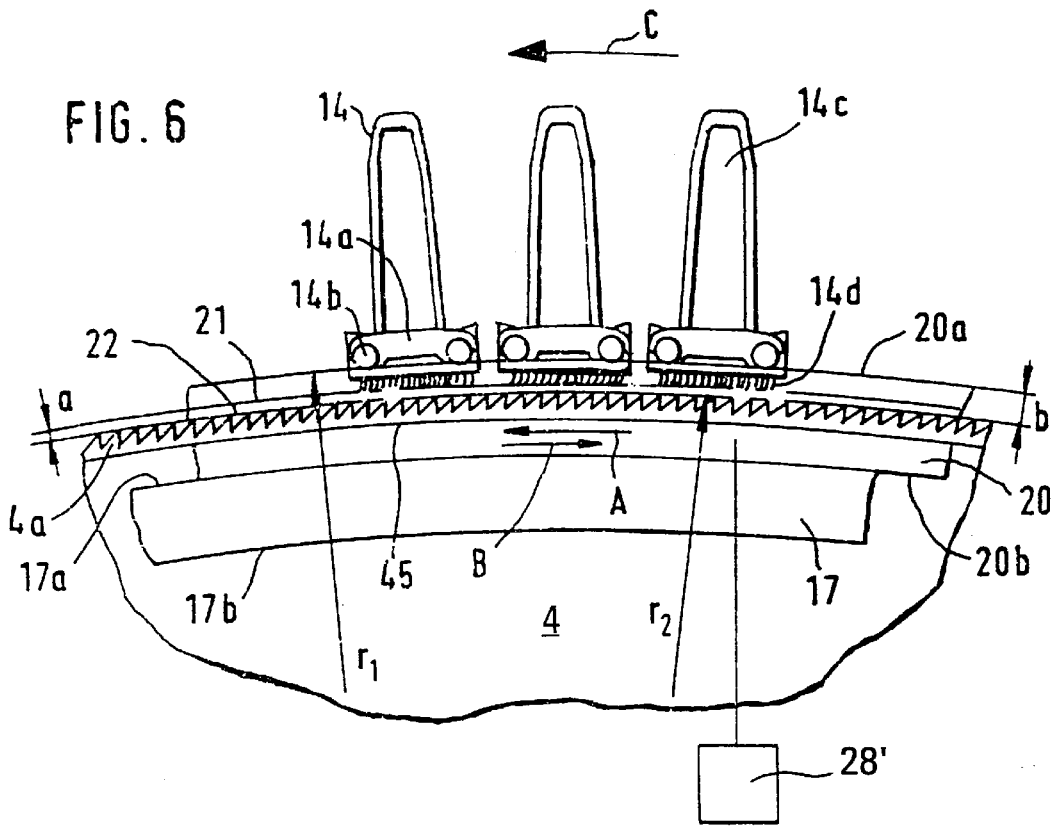
FIG. 6 is a schematic fragmentary side elevational view of a carding cylinder cooperating with flat bars and also showing flexible bends.

The measuring member 24 for automatically detecting the nep number is connected to the electronic control and regulating device (microcomputer) 27 and may be, for example, a NEPCONTROL NCT model, manufactured by Trützschler GmbH & Co. KG. The measuring values for a fiber length which, for example, are determined by a fibrograph, may also be inputted in the electronic control and regulating device 27 by means of an inputting device. Also, a switching element, for example, a push button or the like may be connected to the electronic control and regulating device 27 to activate the drive motor 28. Further, a measuring member, for example, a FLATCONTROL FCT model, manufactured by Trützschler GmbH & Co. KG may be connected to the electronic control and regulating device 27 for detecting the distance a between the points 21 of the flat bar clothings 13d and the points 22 of the cylinder clothing 4a (FIG. 6).

Figure 3:
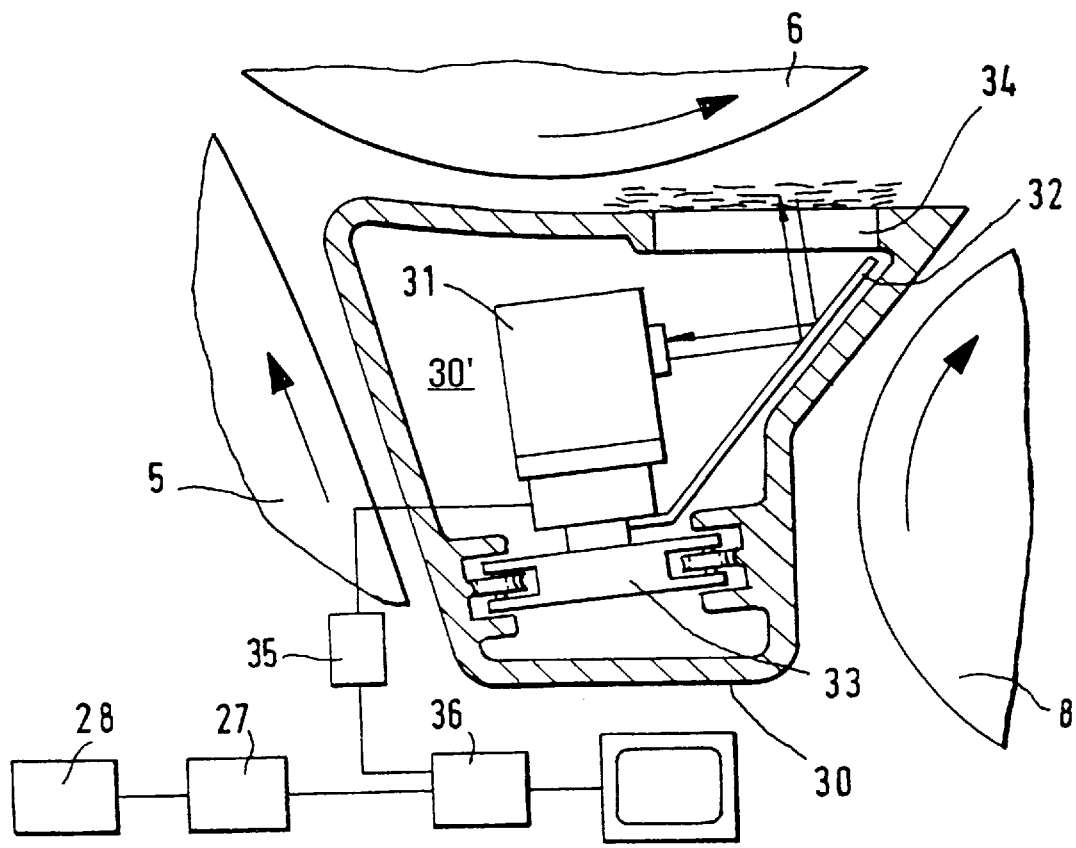
FIG. 3 is a schematic, partially sectional side elevational view of a device positioned underneath the stripping roll of the carding machine for recognizing impurities, such as neps, by means of a camera as well as a block diagram illustrating the connection of the camera to an electronic control and regulating device.

Turning to FIG. 3, underneath the stripper roll 6 a supporting and guiding element 30 is provided, having a cavity 30'. A carriage 33, a camera 31, a non-illustrated illuminating device and a mirror 32, all mounted on the carriage 30 are arranged in the cavity 30'. The supporting and guiding element 30 is provided with a window 34 on which the fiber web runs and whose nep number is detected by the camera 31. The camera 31 is connected with an image processing device 36 via a computer 35. The device 36, in turn, is connected to the control and regulating device 27, an output of which is connected to the motor 28 to thus regulate the speed (and, as a result, the carding intensity) of the carding cylinder 4. As an alternative or as a complementation, a setting member constituted by the motor 28' may be connected to control and regulating device 27 for changing the nep number and the fiber shortening by changing the distance a between the clothings of the flat bars 14 and the clothing of the main carding cylinder 4. It is likewise feasible to regulate in a similar manner the distance of a mote knife from a roll (for example, one or more of the licker-ins 3a, 3b, 3c), or the position of a guide element, or the like.

Figure 4:
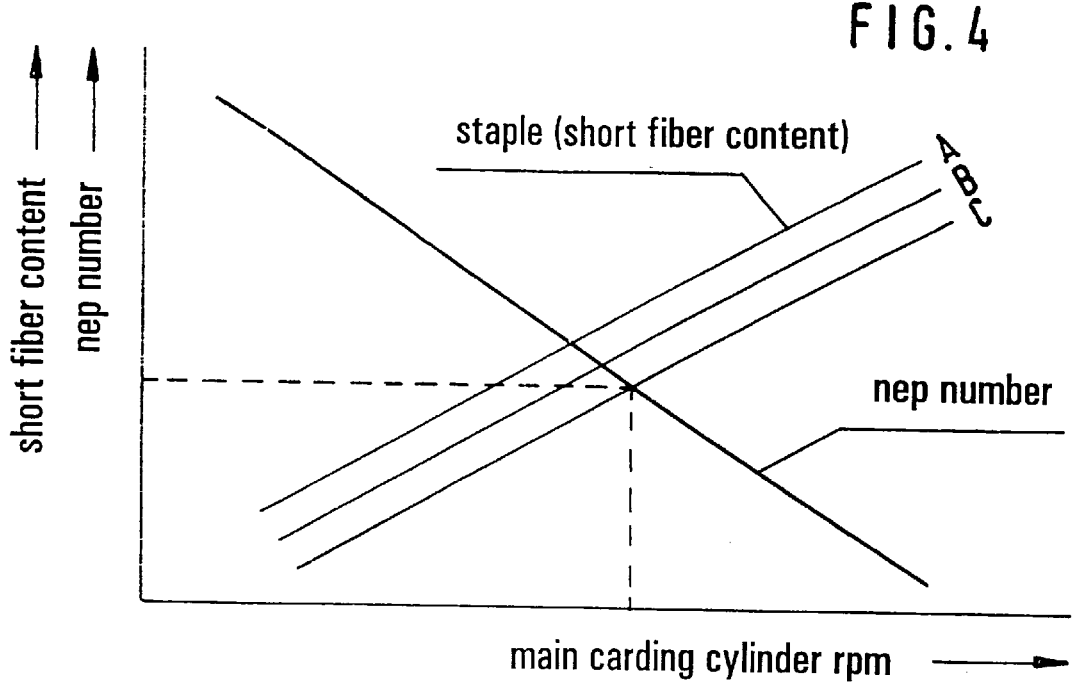
FIG. 4 is a diagram illustrating the short fiber content and nep number as a function of the main carding cylinder rpm for various fiber types.

As shown in the diagram of FIG. 4, as the rpm of the carding cylinder 4 increases, the nep number decreases and the fiber shortening effect increases. The curve for the fiber shortening is shown for fiber types (qualities) A, B and C. The point of intersection between the curves for the nep number and for the fiber shortening determines the optimum nep number and the cylinder rpm associated therewith, as illustrated in broken lines for the fiber type C. Such an optimum is computed and determined in the control and regulating device 27 from the inputted curves of the nep number and the fiber shortening. In this process, a comparison is effected with characteristic curves which are present in the desired value memory 29.

Figure 5:
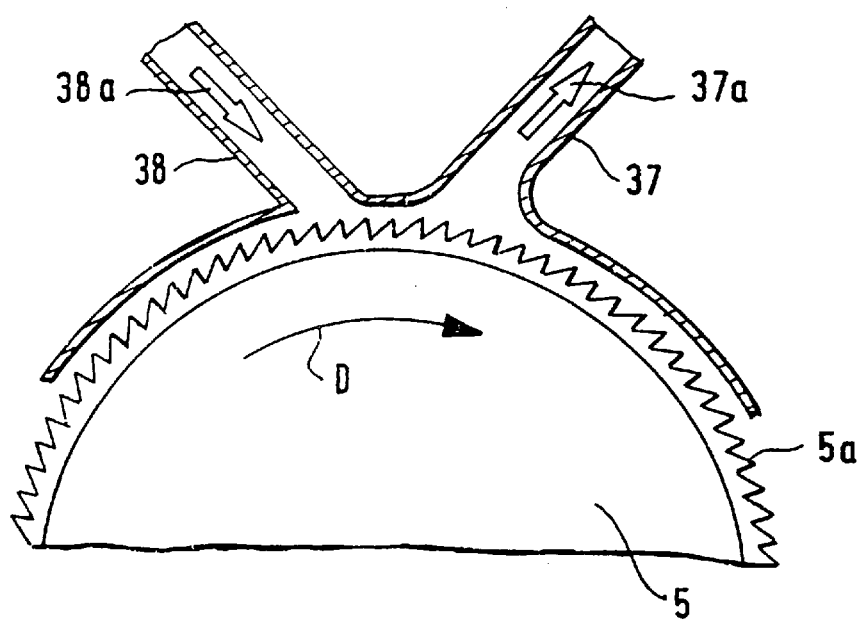
FIG. 5 is a schematic side elevational view of a device for removing small fiber samples from a clothed roll by means of the combined action of a vacuum stream and a compressed air stream.

In FIG. 5, above the doffer 5 a conduit 37 communicates with the space through which fiber material is advanced by the doffer 5. The conduit 37 which is oriented obliquely to the clothing of the doffer 5 is coupled to a non-illustrated vacuum source (such as the intake side of a blower), by means of which a suction stream 37a is generated periodically and at random for entraining small quantities (samples) of fiber from the clothing of the doffer 5. These fibers are subsequently analyzed for determining the fiber length distribution. The fiber quantities drawn away from the doffer 5 are so small that the uniformity of the sliver produced is practically not affected. Based on the sample analysis, a staple diagram or data therefor are generated. Upstream and in the vicinity of the suction conduit 37, as viewed in the rotary direction D, a conduit 38 communicates with the space through which fiber material is advanced by the doffer 5. The conduit 38 is coupled to a non-illustrated air pressure source (such as the output side of a blower), by means of which a compressed air stream 38a is generated which supports the suction effect of the vacuum stream 37a.

Turning to FIG. 6, on each side of the carding machine flexible bends 17 (only one is visible), including a plurality of setting screws, are attached to the frame of the carding machine such that the flexible bends 17 flank an upper peripheral portion of the main carding cylinder 4. Each flexible bend 17 has a convex outer surface 17a and an underside 17b. Above the flexible band 17 a sliding guide 20 is arranged which is made of a low-friction plastic material and which has a convex outer surface 20a and a concave inner surface 20b. The concave inner surface 20b of the sliding guide 20 lies on the convex outer surface 17a of the flexible bend 17 and may slide thereon in the direction of arrows A and B. The flat bars 14 have, at opposite ends, a bar head 14a from which project two axially oriented steel pins 14b which slide on the convex outer face 20a of the sliding guide 20 in the direction of the arrow C. The flat bar clothing 14d is mounted on the underface of the carrier body 14c of the flat bar 14. An imaginary circle contacting the point series of the flat bar clothings 14d is designated at 21. The carding cylinder 4 has on its circumference a cylinder clothing 4a which may be, for example, a sawtooth clothing. An imaginary circle contacting the point series of the cylinder clothings 4a is designated at 22. The distance between the concentric circles 21 and 22 is designated at a and is, for example, 0.20 mm. The distance between the convex outer face 20a and the circle 22 is designated with L. The radius of the convex outer face 20a is designated at $r_1$ whereas the radius of the circle 22 is designated at $r_2$. The radii $r_1$ and $r_2$ intersect in the rotary axis of the main carding cylinder 4. The sliding guide 20 may be shifted in the radial direction $r_1$ by means of a setting member such as the motor 28' to vary the distance a and to thus change the carding intensity.

Figure 7:
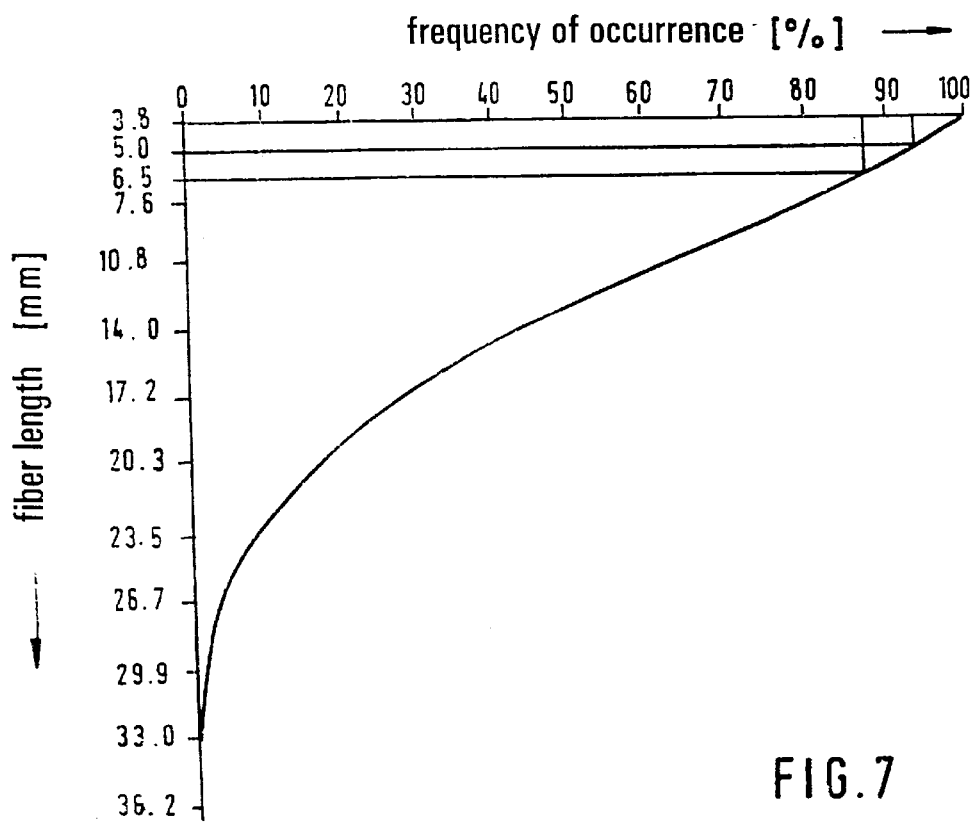
FIG. 7 is a diagram illustrating an occurrence frequency for determining data which are inputted in the control and regulating device for setting the carding intensity.

A sample is removed from the fiber material entrained by the doffer 5 and subjected to an analysis which is to serve subsequently for setting the carding intensity of the carding machine. Such an analysis is performed, for example, with the aid of a fibrograph which generates a fibrogram illustrating the length distribution of the fibers. Such a length distribution is illustrated in the diagram of FIG. 7. The horizontal axis represents the frequency in percentage while the vertical axis indicates the fiber length in mm. The exemplary fibrogram illustrated in FIG. 7 shows that 100% of all fibers have a length of at least 3.8 mm. Approximately 93% of all fibers have a length of more than 5 mm and approximately 88% of all fibers have a length of over 6.5 mm. As further shown by the diagram, the greater the fiber length, the smaller the proportion of the fibers to the entire fiber quantity until eventually, at a fiber length of approximately 35 mm, no more fiber may be found. It was found that fibers shorter than 5 to 6.5 mm do not contribute to the strength of the spun yarn. For this purpose, based on the curve shown in FIG. 7, it is determined how much percentage of all fibers have a length which is less than the set smallest length of 5 to 6.5 mm. The fibrogram shows for 5 mm, for example, that 5% of all fibers are shorter than 5 mm. The curve further shows that 12% of all fibers are shorter than 6.5 mm. The thus-determined 7 to 12% serve, as already indicated above, for setting the carding intensity of the carding machine. The data for the staple diagram are electronically inputted into the control and regulating device 27 which from these data and from data representing the nep number computes an optimum value which serves for setting the carding intensity of the carding machine.

Further, by means of the apparatus and the method according to the invention, for a given carding cylinder rpm a value pair for the short fiber proportion and the nep number may be determined based on the diagram of FIG. 4, externally of the point of intersection of the two curves.

It will be understood that the above description of the present invention is susceptible to various modifications, changes and adaptations, and the same are intended to be comprehended within the meaning and range of equivalents of the appended claims.

What is claimed is:

1. A method of measuring fiber while being processed by a fiber processing machine, comprising the following steps:
    (a) measuring the length of fiber at an inlet of the fiber processing machine;
    (b) measuring the length of fiber at an outlet of the fiber processing machine; and
    (c) forming a difference between the values measured at said inlet and the values measured at said outlet for determining an extent of shortening the fiber is subjected to as the fiber passes through said fiber processing machine.

2. The method as defined in claim 1, further comprising the step of removing a partial fiber quantity from the fiber material; wherein at least one of said measuring steps is performed on the removed partial fiber quantity.

3. The method as defined in claim 2, wherein said step of removing includes the step of generating a suction stream for entraining said partial fiber quantity.

4. The method as defined in claim 3, further comprising the step of generating a stream of compressed air directed into said suction stream for aiding a suction effect thereof.

5. The method as defined in claim 1, wherein said fiber processing machine is a carding machine including a doffer; and further wherein said step (b) is performed at said doffer.

6. The method as defined in claim 1, wherein said fiber processing machine is a carding machine including a stripper roll; and further wherein said step (b) is performed at said stripper roll.

7. The method as defined in claim 1, wherein said fiber processing machine is a carding machine including a pair of cooperating crushing rolls; and further wherein said step (b) is performed in a vicinity of said crushing rolls.

8. The method as defined in claim 1, wherein said fiber processing machine is a carding machine including a licker-in; and further wherein said step (a) is performed at said licker-in.

9. The method as defined in claim 1, further comprising the steps of
    (d) applying input data signals derived from step (c) to a control and regulating device;
    (e) forming, from the input data, optimized machine setting data for the fiber lengths; and
    (f) applying the optimized machine setting data to a fiber length-affecting, adjustable working element of the fiber processing machine.

10. The method as defined in claim 9, wherein the fiber processing machine includes a carding cylinder and flats cooperating with the carding cylinder; wherein said carding cylinder and said flats carry clothings; and further wherein step (f) includes the step of varying the distance between the clothing of the carding cylinder and the clothing of the flats.

11. A fiber processing machine having
    (a) a fiber inlet zone;
    (b) a fiber outlet zone;
    (c) fiber processing components disposed in said inlet and outlet zones and therebetween for consecutively treating fiber as the fiber passes through the fiber processing machine from the inlet zone to the outlet zone;
    (d) first measuring means for measuring lengths of fibers in a fiber mass during passage thereof through said inlet zone;
    (e) second measuring means for measuring lengths of fibers in a fiber mass during passage thereof through said outlet zone; and (f) means for forming differential values from a comparison of measuring values derived from said first and second means for ascertaining a shortening of fiber lengths in the fiber mass.

12. The fiber processing machine as defined in claim 11, further comprising removal means including suction means for removing a sample quantity of fiber from the fiber mass by suction at one of said fiber processing components and for presenting the sample quantity to one of said measuring means.

13. The fiber processing machine as defined in claim 12, wherein said removal means comprises air blast means for assisting said suction means in removing the sample quantity of fiber.

14. The fiber processing machine as defined in claim 11, wherein said fiber processing components include a carding cylinder and flats cooperating with the carding cylinder; wherein said carding cylinder and said flats carry clothings; further comprising setting means for receiving signals representing said differential values and for adjusting a distance between the clothing of the carding cylinder and the clothing of the flats as a function of said differential values.

15. The fiber processing machine as defined in claim 11, wherein said means for forming differential values includes an electronic control and regulating device connected to said first and second measuring means; further comprising setting means connected to said electronic control and regulating device and to said fiber length-affecting, adjustable working element for adjusting said length-affecting, adjustable working element as a function of said differential values.

16. The fiber processing machine as defined in claim 11, wherein said fiber processing components include a carding cylinder and a motor driving said carding cylinder; further comprising means for varying the rpm of said motor to change the rotary speed of said carding cylinder for altering the carding intensity as a function of said differential values.

17. The fiber processing machine as defined in claim 11, further comprising a fibrograph for measuring a fiber length distribution.

18. The fiber processing machine as defined in claim 11, wherein one of said fiber processing components is a doffer; further comprising means for measuring fiber length at said doffer.

19. The fiber processing machine as defined in claim 11, wherein one of said fiber processing components is a doffer-stripping roll; further comprising means for measuring fiber length at said doffer-stripping roll.

20. The fiber processing machine as defined in claim 11, wherein one of said fiber processing components is a licker-in; further comprising means for measuring fiber length at said licker-in.

* * * * *